(12) United States Patent
Lucas et al.

(10) Patent No.: US 11,648,191 B2
(45) Date of Patent: May 16, 2023

(54) METHOD AND COMPOSITION FOR COLOURING AN EYEBROW COMPRISING AN ORGANIC ACID

(71) Applicant: PERACHEM LIMITED, Leeds (GB)

(72) Inventors: Sarah Elizabeth Lucas, Mirfield (GB); John Mama, Leeds (GB); David Malcolm Lewis, Otley (GB)

(73) Assignee: PERACHTM LIMITED, Leeds (GB)

( * ) Notice: Subject to any disclaimer, the term of this patent is extended or adjusted under 35 U.S.C. 154(b) by 125 days.

(21) Appl. No.: 16/963,021

(22) PCT Filed: Nov. 30, 2018

(86) PCT No.: PCT/GB2018/053473
§ 371 (c)(1),
(2) Date: Jul. 17, 2020

(87) PCT Pub. No.: WO2019/141959
PCT Pub. Date: Jul. 25, 2019

(65) Prior Publication Data
US 2020/0337968 A1     Oct. 29, 2020

(30) Foreign Application Priority Data
Jan. 19, 2018     (GB) .................................... 1800877

(51) Int. Cl.
| | | |
|---|---|---|
| *A61K 8/362* | (2006.01) |
| *A61K 8/34* | (2006.01) |
| *A61K 8/365* | (2006.01) |
| *A61K 8/42* | (2006.01) |
| *A61Q 1/10* | (2006.01) |

(52) U.S. Cl.
CPC .............. *A61K 8/362* (2013.01); *A61K 8/347* (2013.01); *A61K 8/365* (2013.01); *A61K 8/42* (2013.01); *A61Q 1/10* (2013.01); *A61K 2800/432* (2013.01); *A61K 2800/59* (2013.01); *A61K 2800/87* (2013.01)

(58) Field of Classification Search
None
See application file for complete search history.

(56) References Cited

U.S. PATENT DOCUMENTS

| | | |
|---|---|---|
| 4,518,614 A | 5/1985 | Parkinson |
| 5,104,413 A | 4/1992 | Ikeda |
| (Continued) | | |

FOREIGN PATENT DOCUMENTS

| | | |
|---|---|---|
| CA | 2613049 A1 | 4/2008 |
| EP | 3159043 A1 | 4/2017 |
| (Continued) | | |

OTHER PUBLICATIONS

PCT International Search Report and Written Opinion for International Application No. PCT/GB2018/053473, dated Feb. 1, 2019, 14 pages.

(Continued)

*Primary Examiner* — Bethany P Barham
*Assistant Examiner* — Barbara S Frazier
(74) *Attorney, Agent, or Firm* — Hoffman Warnick LLC

(57) ABSTRACT

A method of colouring an eyebrow, the method comprising: (i) contacting the eyebrow with a colouring composition comprising: (a) a dye compound; (b) an organic acid; and (c) an aromatic compound.

4 Claims, 3 Drawing Sheets

(56) References Cited

U.S. PATENT DOCUMENTS

| | | |
|---|---|---|
| 6,248,314 B1 | 6/2001 | Nakashimada et al. |
| 7,419,656 B2 | 9/2008 | Hirano |
| 2002/0189031 A1 | 12/2002 | Javet et al. |
| 2004/0231069 A1 | 11/2004 | Carrascal et al. |
| 2008/0292668 A1 | 11/2008 | Baars et al. |
| 2013/0149358 A1* | 6/2013 | Colaco ................ A61K 8/0254 424/70.6 |
| 2017/0354583 A1 | 12/2017 | Goutsis et al. |

FOREIGN PATENT DOCUMENTS

| | | |
|---|---|---|
| FR | 2948871 A1 | 2/2011 |
| FR | 3037238 A1 | 12/2016 |
| GB | 2259717 A | 3/1993 |
| JP | 5489425 B2 | 5/2014 |
| JP | 5647771 B2 | 1/2015 |
| KR | 20080061337 A | 7/2008 |
| WO | 2004108108 A1 | 12/2004 |

OTHER PUBLICATIONS

Great Britain Search Report for Application No. GB1800877.1, dated Oct. 1, 2018, 5 pages.

\* cited by examiner

METHOD AND COMPOSITION FOR COLOURING AN EYEBROW COMPRISING AN ORGANIC ACID

The present invention relates to methods for colouring eyebrows and to compositions for use in the method.

The dyeing of eyebrows is becoming increasingly common for fashion or other purposes. As eyebrows are so prominent it is important to achieve consistent even colour, in a method that is mild to the skin.

It is also desirable to provide a colour which does not fade easily. Furthermore as well as colouring of the hair of the eyebrow it is also desirable in some instances to achieve staining of the skin between the hairs to provide a block of colour.

The present inventors have found a method of colouring eyebrows which provides excellent results.

According to a first aspect of the present invention there is provided a method of colouring an eyebrow, the method comprising:
(i) applying to the eyebrow a colouring composition comprising:
 (a) a dye compound;
 (b) an organic acid; and
 (c) an aromatic compound.

According to a second aspect of the present invention there is provided a colouring composition for colouring eyebrows comprising:
(a) a dye compound;
(b) an organic acid; and
(c) an aromatic compound.

Preferably the method of the first aspect involves contacting the material with a composition of the second aspect.

Preferred features of the first and second aspects will now be described.

The colouring composition comprises a dye compound. Any suitable dye compound may be used.

Preferably the colouring composition comprises a water soluble dye compound containing sulfonate and/or carboxylate groups.

By this we mean that the dye compound includes at least one carboxylate group or at least one sulfonate group.

Such dye compounds may include more than one carboxylate group and/or more than one sulfonate groups.

By carboxylate group we mean to refer to the residue of a carboxylic acid, $-CO_2^-$. By sulfonate group we mean to refer to the residue of a sulfonic acid $-SO_3^-$.

The carboxylate and/or sulfonate groups may be present as the free acid i.e. —COOH or –SO$_3$H. Preferably they are present as the salt of the acid i.e., —COOO$^-$M$^+$ or —SO$_3^-$ M$^+$ where M$^+$ is a cation. Suitable cations include ammonium or substituted ammonium cations, and alkali metal and alkaline earth metal cations. Preferred are alkali metal cations, for example sodium and potassium cations.

The dye compounds of component (a) also include a chromophore. Preferably the dye compound includes a chromophore that is active in the visible region of the electromagnetic spectrum. However dye molecules including a chromophore that is active in the ultraviolet or infrared region of the electromagnetic spectrum are also within the scope of the invention.

The dye compounds of component (a) include a fully formed chromophore that is present when the composition is prepared. It is not formed in situ.

The dye compounds used in the colouring composition may include dye compounds generally known to those skilled in the art of textile dyeing as acid dyes, including the classes of acid milling dyes and acid levelling dyes, although the hair cosmetic industry labels these as direct dyes.

Acid dyes are typically water soluble anionic dyes that contain one or more sulphonic acid groups, usually as the sodium salt, carboxylic acid groups or hydroxyl groups (less common). The structure on which the dyes are based depends on the colour. Acid dyes can be based on a number of chromophores, which tend to dictate the colour of the dye. For example, blue acid dyes are often based on an anthraquinone moiety, or triphenylmethane, although some may be azo based, formazan or phthalocyanine based. Red, orange and yellow acid dyes tend to be based upon azo moieties, although Acid Yellow 3 includes a quinoline chromophore.

Compounds based on stilbene, coumarin or xanthene including carboxylate and/or sulfonate residues may be useful in compositions for providing special effects. Such compounds are known to be fluorescent.

In some preferred embodiments the dye compounds used in the colouring compositions do not include any transition metals.

In some preferred embodiments the dye compounds used in the colouring compositions do not include any chelated metal species.

The Colour Index International is a standard classification system for dyes and pigments which contains historic, proprietary, generic names and generic numbers that have been applied to colours. It was first published in 1924 and has been updated and reprinted since. The $2^{nd}$ (1956), $3^{rd}$ (1971) and $4^{th}$ (2002) editions are jointly published and maintained by the Society of Dyers and Colourists (SDC) (UK) and American Association of Textile Chemists and Colourists (AATCC). The structures of the dye compounds shown in this specification are taken from the Colour Index International.

Examples of suitable dyes for use in the colouring composition contacted with the material in step (i) of the method of the present invention include the following:

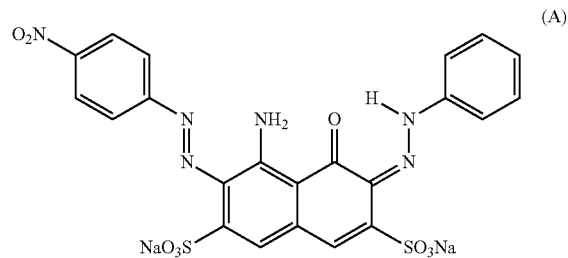

(A)

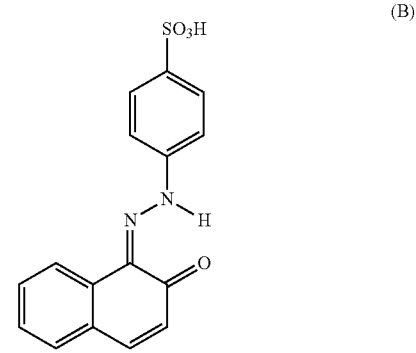

(B)

-continued
(C)
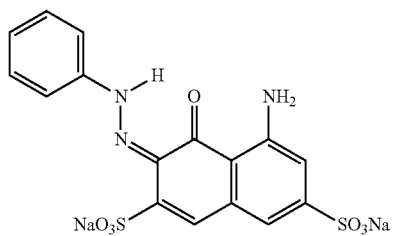
(D)
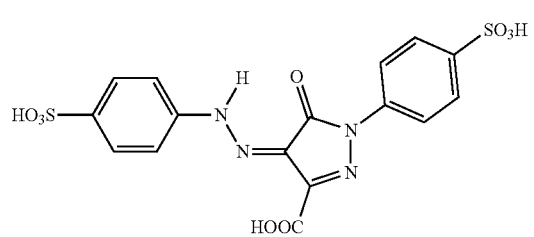
(E)
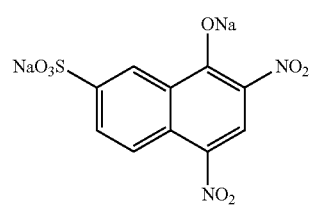
(F)
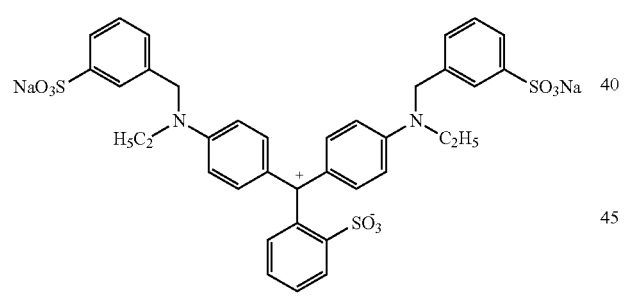
(G)
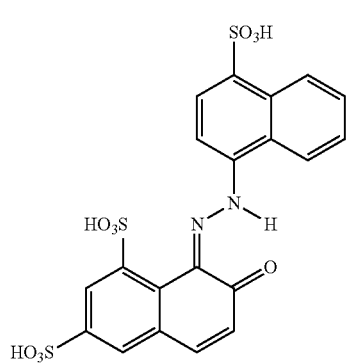
-continued
(H)
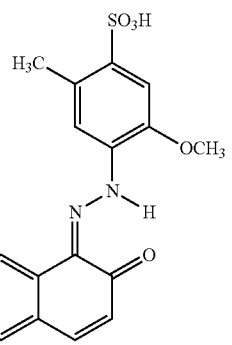
(I)
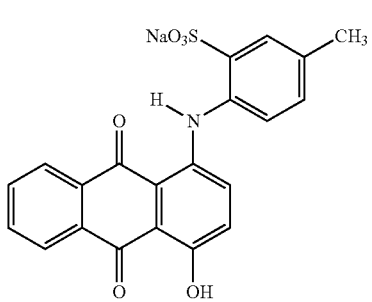
(J)
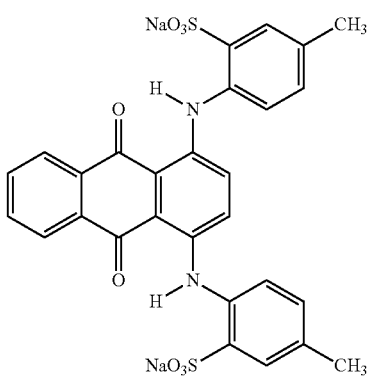
(K)
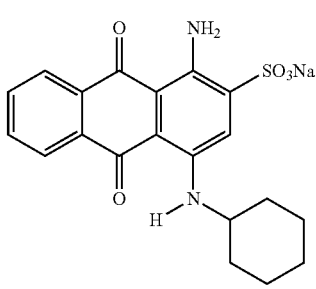
(L)
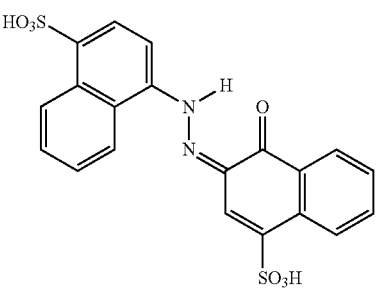

(M)
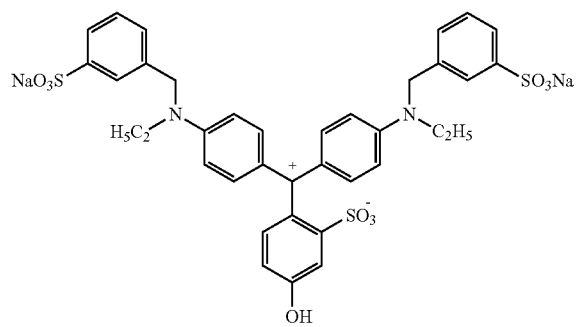
(N)
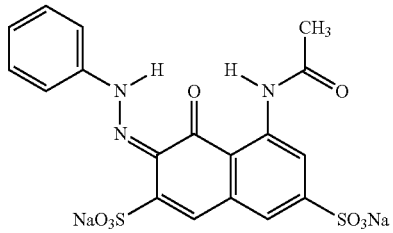
(O)
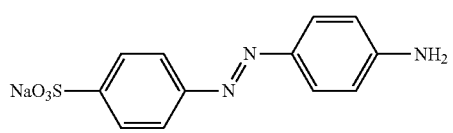
(P)
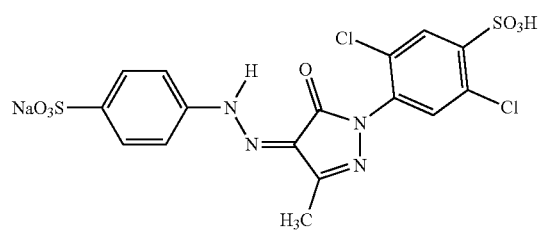
(Q)
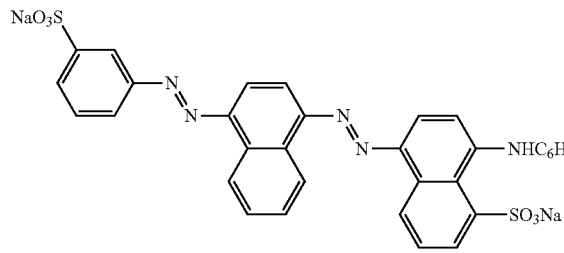
(R)
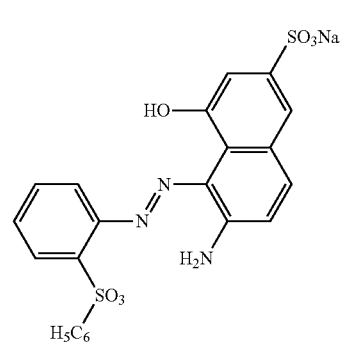
(S)
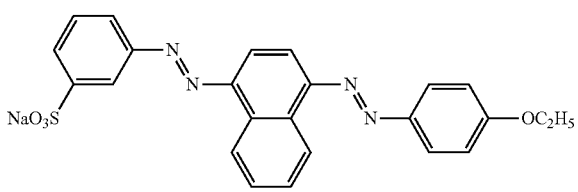
(T)
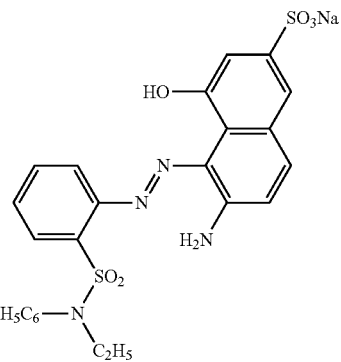
(U)
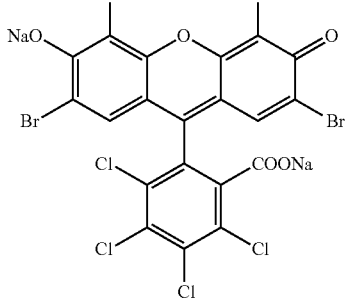
(V)
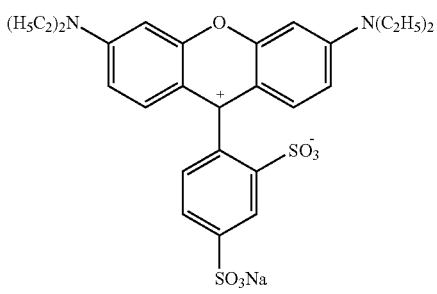
(W)
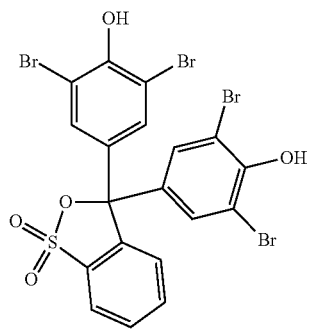

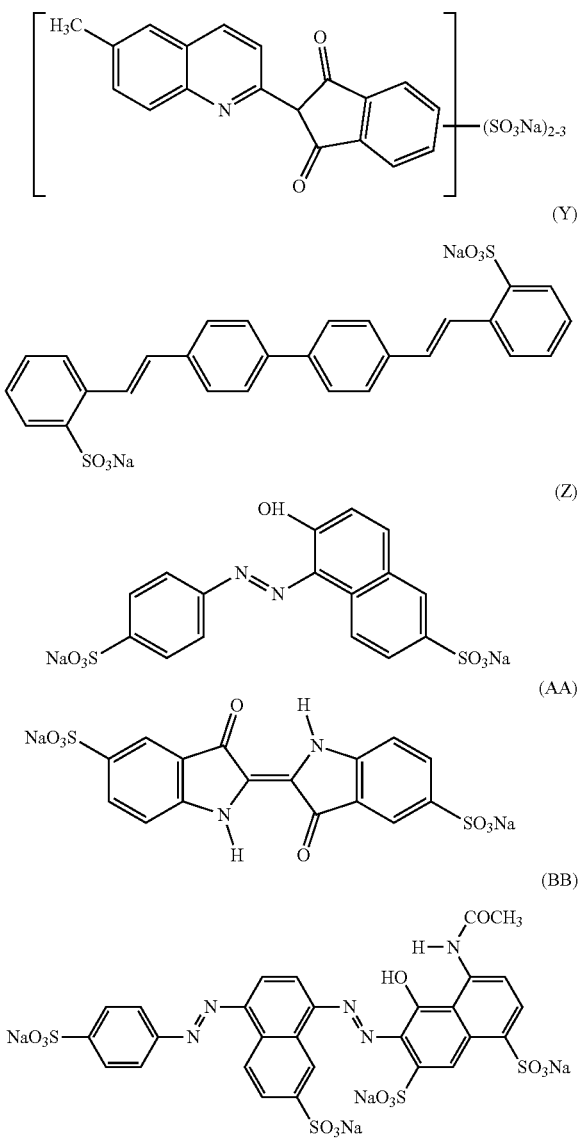

Compound (A) is known as CI Acid Black 1, Duramine Black 10B and Black-Blue 10B.

Compound (B) is known as CI Acid Orange 7 and Duramine Orange II.

Compound (C) is known as CI Acid Red 33 and D&C Red 33.

Compound (D) is known as CI Acid Yellow 23, Acid Tartrazine and Eurogran tartrazine.

Compound (E) is known as CI Acid Yellow 1, Ext D&C Yellow 1 and Naphthol Yellow S.

Compound (F) is known as CI Acid Blue 9, Duracol Brilliant Blue FCF E133, CI Food Blue 2 and FD&C Blue 1.

Compound (G) is known as CI Acid Red 18, Duracol Ponceau 4R E124 and Eurocert Ponceau 4R.

Compound (H) is known as CI Food Red 17 and FD&C Red 40.

Compound (I) is known as CI Acid Violet 43 and Ext. D&C Violet 2.

Compound (J) is known as CI Acid Green 25 and D&C Green 5.

Compound (K) is known as CI Acid Blue 62, Acid Brilliant Blue R and Duramine Blue R.

Compound (L) is known as CI Acid Red 14, CI Food Red 3 and Duracol Carmoisine.

Compound (M) is known as CI Food Green 3 and D&C Green 3.

Compound (N) is known as CI Acid Red 1 and Lissamine Red 2G.

Compound (O) is known as CI Direct Orange 39 and Solar Orange 2GL.

Compound (P) is known as CI Acid Yellow 17, Duramine Yellow 2G and Acrolan Yellow 2G.

Compound (Q) is known as CI Acid Blue 113 and Telon Navy AMF.

Compound (R) is known as CI Acid Red 42, Telon Red BN and Acidol Red 2BE-NW.

Compound (S) is known as CI Acid Orange 127 and Nylosan Orange N-RL.

Compound (T) is known as CI Acid Red 57 and Duramine Red 3G.

Compound (U) is known as CI Acid Red 92 and D&C Red 28.

Compound (V) is known as CI Acid Red 52, Acid Rhodamine B and Nylosan Rhodamine B.

Compound (W) is known as Tetrabromophenol Blue.

Compound (X) is known as CI Acid Yellow 3 and D&C Yellow 10.

Compound (Y) is known as disodium distyryl biphenyl disulfonate, VI bright SX powder and Tinopal CBS.

Compound (Z) is known as CI Food Yellow 3 and Sunset Yellow FCF.

Compound (AA) is known as Acid Blue 74 and Indigo Carmine.

Compound (BB) is known as Food Black 1 and E151.

The names given above represent a non-exhaustive list and compounds having the structures shown may also be known by other names. Although the above mentioned trade names may change, the skilled person would be able to consult the Colour Index International to identify the dye compound and find a current manufacturer.

Preferred dyes for use herein are those approved for use in cosmetic formulations.

Suitable dyes for use in colouring compositions described herein may be selected from those specified on the INCI list (International Nomenclature of Cosmetic Ingredients list). This is drawn up by the Scientific Committee on Consumer Products (SCCP) managed by the Directorate-General for Health and Consumer Protection of the European Commission. The SCCP approve a list of chemicals for use in cosmetics which is referred to as the INCI list.

The colouring compositions of the present invention may include a mixture of two or more dye compounds. Mixtures of dyes may be combined in a specific ratio to achieve a desired colour or other visual effect.

Preferably component (a) comprises one or more dye compounds selected from:
  Acid Red 18 (the compound of formula (G));
  Acid Blue 74 (the compound of formula (AA));
  Food Black 1 (the compound of formula (BB));
  Acid Red 33 (the compound of formula (C));
  Acid Blue 62 (the compound of formula (K));
  Acid Black 1 (the compound of formula (A));
  Acid Red 92 (the compound of formula (U));
  Acid Green 25 (the compound of formula (J));
  Acid Violet 43 (the compound of formula (I));
  Acid Red 14 (the compound of formula (L));
  Acid Yellow 3 ((the compound of formula (X));

Food Yellow 3 (the compound of formula (Z));
Acid Yellow 23 (the compound of formula (D));
Acid Blue 9 (the compound of formula (F)); and
Food Red 17 (the compound of formula (H)).

Preferably component (a) comprises one or more dye compounds selected from:
Acid Green 25 (the compound of formula (J));
Acid Violet 43 (the compound of formula (I));
Acid Red 14 (the compound of formula (L));
Food Black 1 (the compound of formula (BB));
Acid Yellow 3 ((the compound of formula (X));
Food Yellow 3 (the compound of formula (Z));
Acid Yellow 23 (the compound of formula (D));
Acid Blue 9 (the compound of formula (F)); and
Food Red 17 (the compound of formula (H)).

In some preferred embodiments component (a) comprises one or more dye compounds selected from:
Acid Yellow 23 (the compound of formula (D));
Acid Blue 9 (the compound of formula (F));
Food Red 17 (the compound of formula (H)); and
Acid Green 25 (the compound of formula (J)).

The colouring composition preferably comprises at least 0.0001 wt % of the dye compound. Preferably it comprises at least 0.001 wt %, more preferably at least 0.01 wt %, suitably at least 0.05 wt %.

The colouring composition suitably comprises up to 40 wt % of the dye compound, preferably up to 30 wt %, more preferably up to 25 wt %, suitably up to 20 wt %, preferably up to 15 wt %, more preferably up to 12 wt %, for example up to 10 wt %, up to 7 wt %, up to 5 wt % or up to 3 wt %.

Commonly the composition of the present invention comprises a mixture of two or more dye compounds. The above amounts refer to the total amounts of all dye compounds present in the composition.

Suitably dyes are present in the composition in a total amount of from 0.05 to 3 wt %, suitably 0.1 to 2.5 wt %, for example 0.25 to 2 wt % or 0.5 to 1.5 wt %.

Preferably the colouring composition of the present invention comprises less than 1 wt % oxidative dye compounds or precursors thereof.

Oxidative hair dyes are well known and the skilled person will recognise the types of compounds used. It will be appreciated that the precise nature of the coloured species present in the hair is often not clear since they are formed in situ by treatment of the hair with one or more precursor compositions (suitably containing an aromatic amine and a coupler compound) and an oxidising composition. Typically when hair is oxidatively dyed an aromatic amine composition and a coupler are mixed with a developer immediately before application to the hair. The developer is usually an oxidising composition containing for example hydrogen peroxide. The aromatic amine and coupler precursor compositions comprise small aromatic compounds which interact in the presence of the oxidising developer to form large aromatic conjugated species which are coloured. Although these compounds are referred to as "hair dyes", the resulting coloured species may more correctly be referred to as pigments since they are usually water insoluble.

By oxidative dye compounds or precursors thereto we mean to refer to the compounds formed during the oxidative dyeing process or the precursor aromatic amine or coupler compounds.

Preferably the colouring composition of the present invention comprises less than 0.1 wt % oxidative dye compounds or precursors thereof, preferably less than 0.01 wt %, more preferably less than 0.001 wt %, preferably less than 0.0001 wt %.

Preferably the composition does not comprise any oxidative dye compounds or precursors thereof.

The colouring composition comprises (b) an organic acid. Preferably component (b) comprises an organic acid which is not an aromatic acid. Suitably component (b) comprises an aliphatic organic acid.

Suitable organic acids include acetic acid, tartaric acid, citric acid, glycolic acid, lactic acid, malic acid, maleic acid, succinic acid, malonic acid and 3-hydroxypropanoic acid.

Some preferred organic acids are hydroxy substituted organic acids and dicarboxylic acids.

Some especially preferred organic acids are polycarboxylic acids.

Preferred organic acids include tartaric acid, succinic acid, citric acid, glycolic acid, lactic acid, malic acid and 3-hydroxypropanoic acid.

One preferred organic acid is lactic acid.

Most preferably the organic acid is citric acid.

The organic acid is suitably present in an amount of at least 0.1 wt %, preferably at least 0.5 wt %, preferably at least 1 wt %. In some embodiments the organic acid may be present in an amount of at least 2 wt %, for example at least 2.5 wt %, or at least 3 wt %.

In some preferred embodiments lower amounts may be included.

The organic acid is suitably present in an amount of up to 20 wt %, suitably up to 15 wt %, preferably up to 10 wt %, more preferably up to 8 wt %, preferably up to 6 wt %, suitably up to 5.5 wt %, preferably up to 5 wt %.

Most preferably the organic acid is present in an amount of from 0.5 to 5 wt %, preferably 1 to 3 wt %, more preferably 1.5 to 2.5 wt %.

Component (b) may comprise a mixture of two or more organic acids, for example two or more aliphatic organic acids. In such embodiments the above amounts refer to the total of all such organic acids present in the composition.

Suitably the organic acids are present in the composition in a total amount of from 0.1 to 10 wt %, suitably 0.5 to 5 wt %, for example 1 to 4 wt %.

The colouring composition further comprises (c) an aromatic compound.

Preferred aromatic compounds include aromatic acids and aromatic alcohols.

By aromatic acids we mean to refer to any compound which includes an aromatic moiety and a carboxylic acid moiety, i.e. a group COOH.

By aromatic alcohol we mean to refer to any compound which includes an aromatic moiety and a hydroxy group.

In some embodiments component (c) comprises an aromatic acid. This component is separate and present in addition to the organic acid of component (b).

Suitable aromatic acids include benzoic acid, cinnamic acid and phthalic acid (including ortho or para phthalic acid).

One preferred aromatic acid is benzoic acid.

In some embodiments component (c) comprises an aromatic alcohol.

Suitable aromatic alcohols include benzyl alcohol, benzyloxyethanol and 1,3-benzenedimethanol.

In some embodiments component (c) comprises an aromatic acid and an aromatic alcohol.

Preferably the aromatic compound is present in an amount of at least 0.1 wt %, preferably at least 1 wt %, more preferably at least 3 wt %, suitably at least 5 wt %, for example at least 6 wt %.

Preferably the aromatic compound may be present in an amount of up to 50 wt %, suitably up to 30 wt %, preferably up to 25 wt %, more preferably up to 20 wt %, suitably up to 15 wt %, for example up to 12 wt % or up to 10 wt %.

In embodiments in which a mixture of two or more aromatic compounds are present the above amounts refer to the total of all such aromatic compounds present in the composition.

Suitably aromatic compounds are present in the composition in a total amount of 1 to 20 wt %, preferably 3 to 15 wt %, suitably 5 to 12 wt %.

Preferably component (c) is benzyl alcohol.

Preferably the colouring composition comprises from 0.1 to 20 wt % of an aromatic alcohol, preferably benzyl alcohol, preferably from 1 to 15 wt %, more preferably from 5 to 10 wt %.

In some preferred embodiments the colouring composition further comprises (d) an alcohol.

Suitably component (d) comprises an alcohol which is not an aromatic alcohol. Suitably component (d) comprises an aliphatic alcohol.

Preferred alcohols are water miscible alcohols.

Suitably the alcohol is a monohydric alcohol.

Preferably the alcohol is a $C_1$ to $C_4$ alcohol.

Suitably the alcohol is selected from ethanol, n-propanol, isopropanol, butanol and mixtures thereof.

Preferably the alcohol is isopropanol and/or ethanol.

Most preferably component (d) comprises ethanol.

Suitably component (d) is ethanol.

The alcohol is preferably present in an amount of at least 1 wt %, preferably at least 3 wt %, preferably at least 5 wt %, suitably at least 8 wt %, preferably at least 10 wt %, more preferably at least 12 wt %, suitably at least 15 wt %, for example at least 17 wt % or at least 18 wt %.

The alcohol is suitably present in an amount of up to 80 wt %, suitably up to 70 wt %, preferably up to 50 wt %, more preferably up to 40 wt %, preferably up to 35 wt %, suitably up to 30 wt %, preferably up to 25 wt %, for example up to 23 wt %.

In embodiments in which a mixture of two or more alcohols are present the above amounts refer to the total of all such alcohols present in the composition.

Suitably alcohols are present in the composition in a total amount of from 5 to 40 wt %, preferably 10 to 30 wt %, for example 15 to 25 wt %.

In some preferred embodiments the colouring composition further comprises (e) a thickener.

Any suitable thickener may be used.

Suitable thickeners include those mentioned on the INCI list.

Preferred thickeners are water soluble thickeners.

Suitable thickeners include natural thickeners and synthetic compounds.

Suitable synthetic thickeners include, for example, polyacrylate thickeners.

Preferred thickeners are natural thickeners, especially polysaccharide based thickeners.

Suitable polysaccharide based thickeners include xanthan gum, guar gum, alginates and cellulose based thickeners.

One especially preferred thickener for use herein is tylose.

The thickener is suitably present in an amount of at least 0.1 wt %, preferably at least 0.25 wt %, preferably at least 0.5 wt %, suitably at least 0.75 wt %, preferably at least 1 wt %.

The thickener is suitably present in an amount of up to 20 wt %, suitably up to 15 wt %, preferably up to 10 wt %, more preferably up to 5 wt %, preferably up to 3 wt %, preferably up to 2 wt %.

The colouring composition may comprise a mixture of two or more thickeners. In such embodiments the above amounts refer to the total of all thickeners present in the composition.

Suitably thickeners are present in the composition in a total amount of from 0.1 to 5 wt %, suitably 1 to 3 wt %.

Preferably the colouring composition comprises an emulsifier. The emulsifier is suitably present in an amount of from 0.01 to 5 wt %, for example 0.1 to 1 wt %. Suitably emulsifiers are known to the person skilled in the art.

One preferred emulsifier for use herein is sold under the trade mark Heliogel by Lucas Meyer Cosmetics. This material comprises a mixture of sodium acrylate copolymers, hydrogenated polyisobutene, phospholipids phospholipids, polyglyceryl 10 stearate and sunflower oil.

In some preferred embodiments the colouring composition further comprises urea. Urea is suitably present in an amount of at least 0.1 wt %, suitably at least 0.5 wt %.

Urea may be present in an amount of up to 5 wt %, preferably up to 2 wt %.

In some preferred embodiments the colouring composition comprises 0.1 to 2 wt % urea.

In some preferred embodiments the colouring composition further comprises a preservative compound. Suitable preservative compounds are known to the person skilled in the art and include phenoxyethanol, potassium sorbate, ethyl hexyl glycerine, sodium benzoate, parabens and isothiazolinones.

One especially preferred preservative compound for use herein is phenoxyethanol.

The preservative compound is preferably present in an amount of from 0.01 to 5 wt %, preferably 0.1 to 2 wt %. Mixtures of two or more preservative compounds may be present.

In some embodiments the composition may further comprise a humectant. Suitably humectants are known to the person skilled in the art and include, for example glycerol.

The humectant is suitably present in an amount of from 0.01 to 5 wt %, for example 0.1 to 2 wt %. Mixtures of two or more humectants may be used.

Preferably the colouring composition comprises citric acid.

Preferably the composition comprises 0.1 to 10 wt %, preferably 1 to 3 wt % citric acid.

Preferably the composition comprises benzyl alcohol.

Preferably the composition comprises 1 to 20 wt %, preferably 5 to 10 wt % benzyl alcohol.

Preferably the composition comprises ethanol.

Preferably the composition comprises 5 to 50 wt %, preferably 10 to 30 wt % ethanol.

The colouring composition preferably comprises less than 0.1 wt % thiourea. Preferably the colouring composition does not comprise thiourea.

Preferably the composition of the present invention comprises less than 1 wt % thiol, preferably less than 0.1 wt %, more preferably less than 0.01 wt %, preferably less than 0.001 wt %.

The colouring composition preferably does not comprise a thiol.

Apart from the dye compounds, the composition of the present invention preferably comprises less than 1 wt % of sulfur-containing compounds, preferably less than 0.1 wt %, more preferably less 0.01 wt %, preferably less than 0.001 wt %.

The colouring composition preferably does not contain any sulfur-containing compounds other than the dye compounds.

Suitably the colouring composition of the present invention comprises less than 1 wt % polysiloxanes, preferably less than 0.1 wt %, more preferably less than 0.01 wt %, preferably less than 0.001 wt %.

The colouring composition of the present invention does not contain any polysiloxane compounds.

Apart from the dye compounds, the composition of the present invention preferably comprises less than 1 wt % carbonate compounds, preferably 0.01 wt %, more preferably less than 0.001 wt %, preferably less than 0.0001 wt %. Suitably the colouring composition of the present invention does not comprise any carbonate compounds, for example ethylene carbonate or propylene carbonate, other than the dye compounds.

Preferably the colouring composition of the present invention comprises less than 1 wt % pyrrolidone compounds, preferably less than 0.1 wt %, more preferably less than 0.01 wt %, preferably less than 0.001 wt %.

Preferably the composition of the present invention does not comprise any pyrrolidone compounds.

Preferably the colouring composition of the present invention comprises less than 1 wt % peroxide compounds, preferably less than 0.01 wt %, more preferably less than 0.001 wt %, preferably less than 0.0001 wt %.

Preferably the composition does not comprise any peroxide compounds.

Preferably the composition of the present invention comprises less than 1 wt % lactones, preferably less than 0.01 wt %, more preferably less than 0.001 wt %, preferably less than 0.0001 wt %.

Preferably the composition does not comprise any lactones.

Suitably the composition of the present invention comprises less than 1 wt % ammonia preferably less than 0.01 wt %, more preferably less than 0.001 wt %, preferably less than 0.0001 wt %.

Preferably the composition does not comprise any ammonia.

Suitably the composition of the present invention comprises less than 1 wt % pigments preferably less than 0.01 wt %, more preferably less than 0.001 wt %, preferably less than 0.0001 wt %.

Preferably the composition does not comprise any pigments.

Suitably the composition of the present invention comprises less than 1 wt % iron compounds preferably less than 0.01 wt %, more preferably less than 0.001 wt %, preferably less than 0.0001 wt %.

Preferably the composition does not comprise any iron compounds.

Suitably the composition of the present invention comprises less than 1 wt % transition metal compounds preferably less than 0.01 wt %, more preferably less than 0.001 wt %, preferably less than 0.0001 wt %.

Preferably the composition does not comprise any transition metal compounds.

In some preferred embodiments the colouring composition comprises:
 a) a dye compound;
 b) an organic acid;
 c) benzyl alcohol; and
 d) a $C_1$ to $C_4$ monohydric alcohol.

In a preferred embodiment the colouring composition comprises:
 a) a dye compound containing sulfonate and/or carboxylate groups;
 b) citric acid;
 c) benzyl alcohol; and
 d) at least 10 wt % ethanol.

In some especially preferred embodiments the colouring composition comprises:
 a) 0.1 to 5 wt % of one or more dye compounds containing sulfonate and/or carboxylate groups;
 b) 0.1 to 10 wt % citric acid;
 c) 10 to 30 wt % ethanol; and
 d) 5 to 15 wt % benzyl alcohol.

In some especially preferred embodiments the colouring composition comprises:
 a) 0.5 to 2 wt % of one or more dye compounds containing sulfonate and/or carboxylate groups;
 b) 1 to 4 wt % citric acid;
 c) 15 to 25 wt % ethanol; and
 d) 5 to 10 wt % benzyl alcohol.

In some especially preferred embodiments the colouring composition comprises:
 a) 0.5 to 2 wt % of one or more dye compounds containing sulfonate and/or carboxylate groups;
 b) 1 to 4 wt % citric acid;
 c) 15 to 25 wt % ethanol;
 d) 5 to 10 wt % benzyl alcohol; and
 e) 0.1 to 3 wt % urea.

In some especially preferred embodiments the colouring composition comprises:
 a) 0.5 to 2 wt % of one or more dye compounds containing sulfonate and/or carboxylate groups;
 b) 1 to 4 wt % citric acid;
 c) 15 to 25 wt % ethanol;
 d) 5 to 10 wt % benzyl alcohol;
 e) 0.1 to 3 wt % urea; and
 f) 0.1 to 2 wt % phenoxyethanol.

The colouring composition may comprise one or more further ingredients for example colourants, fragrances, emollients, pH adjusting agents, surfactants and chelating agents. The selection of such components is within the competence of the skilled person in the art.

The colouring composition is preferably an aqueous composition. Suitably it comprises at least 20 wt % water, preferably at least 30 wt % water, more preferably at least 40 wt %, suitably at least 50 wt %, preferably at least 60 wt %.

Suitably water, ethanol and benzyl alcohol together comprise at least 80 wt %, preferably at least 90 wt %, more preferably at least 95 wt % of all solvents present in the composition.

Suitably water and ethanol together comprise at least 80 wt % of all solvents present in the composition.

Preferably the colouring composition is acidic.

Preferably the colouring composition has a pH of from 1 to 6, suitably from 2 to 5, preferably from 2.5 to 4.5, more preferably from 3 to 4.

The composition may suitably comprise one or more pH adjusting agents. Suitable compounds of this type will be known to the person skilled in the art. Preferred pH adjusting agents include sodium hydroxide and aminomethyl propanol.

In some embodiments the colouring composition may be prepared immediately prior to application to the eyebrows, for example from two or more precursor compositions. Compositions of this type are known to the person skilled in the art and allow components that may interact with each other to be stored separately to increase the shelf life of the product.

However in preferred embodiments the colouring composition is provided as a single ready to use fully formulated composition. Advantageously the colouring composition of the present invention is shelf stable. Suitably it does not chemically or physically degrade on storage under ambient conditions for more than six months.

The colouring composition is suitably in the form of a gel or paste.

It suitably has a consistency that enables it to be stirred. Suitably the composition may be easily applied to the eyebrows but once in position it does not drip or run.

The colouring composition may be applied to the eyebrows by any suitable means.

The composition may suitably be massaged or rubbed onto the eyebrows or brushed onto the eyebrows.

In some embodiments the composition is applied by a brush or other applicator.

The composition may be provided in a pot or tube in which the applicator may be dipped and then used to apply the composition to the eyebrows.

In some embodiments the composition may be provided in a container which includes an applicator, through which it passes, for example a pen-type device.

After application the composition may be spread across the brow using fingers and/or an applicator.

Any composition which is accidentally spread onto the skin around the eyebrows is suitably wiped away.

In some embodiments the method of the present invention is used to colour eyebrows that have been previously dyed and/or bleached. In such embodiments the hair may be damaged.

It has been advantageously found that excellent dyeing can be achieved at ambient temperature.

The colouring composition is preferably contacted with the eyebrows for a period of at least 0.1 minute, preferably at least 0.5 minutes, more preferably at least 1 minute.

The composition may be contacted with the eyebrows for a period of up to 2 hours, suitably up to 1 hour, preferably up to 30 minutes, for example up to 15 minutes. A contact time of 2 to 10 minutes is especially preferred.

Suitably the method of the third aspect includes a step (ii) or removing the composition from the eyebrow.

At the end of the contact time the composition may be wiped from the eyebrows. This may be carried out using a tissue, cotton pad or other wipe.

In some embodiments the composition may be rinsed away with water or mild soap solution.

According to a third aspect there is provided a kit comprising a composition of the second aspect and means for applying the composition to the eyebrow.

Any suitable means for applying the composition to the eyebrows may be provided, such as is described above.

In some embodiments the kit may comprise a device comprising a reservoir containing the colouring composition and means for applying the composition to the eyebrow. Suitably the reservoir and means for applying the composition to the eyebrow (an application means) are part of the same single device.

Suitably the device comprises a reservoir connected to an application means.

The application means suitably comprises a narrow opening through which the composition can be applied directly onto the eyebrow. In some embodiments a brush or fibres may be provided at the opening to assist with application of the composition.

The kit of the third aspect may further comprise a means for removing the composition from the eyebrows. This may be a wipe, tissue or cotton pad. In some embodiments a rinsing composition may be provided, optionally with means for applying the rinsing solution. Such a rinsing solution would be an aqueous composition comprising mild surfactants, typically non-ionic and/or anionic surfactants.

In some embodiments the kit may further comprise a clean-up solution. This can be used to remove any excess colouring which is unintentionally applied or spilled onto a part of the skin and/or hair which is it not desired to be coloured. For example the composition may be accidentally applied to an area of skin around the brow where skin staining would not be desirable. Application of the clean-up solution could remove the composition from this area and prevent staining.

The clean-up solution is preferably an aqueous based system which comprises up to 40 wt % of a water miscible alcohol, for example 5 to 35 wt %, or 10 to 30 wt % ethanol. The clean-up solution typically comprises a mixture of surfactants (preferably non-ionic and/or anionic surfactants), suitably in an amount of up to 10 wt %, preferably 0.1 to 5 wt %. The clean-up solution suitably is preferably alkaline. Suitably it has a pH of more than 8, preferably from 9 to 11.

The kit may further comprise instructions for use.

Suitably eyebrows dyed according to the method of the first aspect of the present invention are dyed evenly and consistently.

Advantageously as well as colouring hair, the composition also stains the skin between the hairs of the eyebrow. This provides a strong block of colour which users find highly desirable.

Preferably the method of the first aspect provides a method of colouring the hairs of an eyebrow and the skin therebetween, the method comprising:
 (i) applying to the eyebrow a colouring composition comprising:
  (a) a dye compound;
  (b) an organic acid; and
  (c) an aromatic compound.

Suitably eyebrows dyed according to the present invention have excellent wash fastness.

Suitably eyebrows coloured by the method of the present invention shows substantially no fading after 5 washes of the face, preferably after 10 washes, suitably after 15 washes, more preferably after 20 washes of the face.

The method of the second aspect of the present invention may be regarded as a method of "permanently" dyeing eyebrows.

The colouring composition and method have been found to provide excellent dyeing of eyebrows. In particular eyebrows coloured according to the invention are dyed evenly and deep dyeings are achieved even when colouring eyebrows that have been previously bleached and/or dyed.

According to a fourth aspect of the present invention there is provided the use of a composition comprising:
 (a) a dye compound;
 (b) an organic acid; and
 (c) an aromatic compound;
to colour eyebrows.

Preferred features of the fourth aspect are as defined in relation to the first and/or second aspects.

Suitably the use of a third aspect provides an even and consistent colour.

It was found by the applicant that for some compositions, discolouration could occur after application to the eyebrow upon drying. However this does not occur when using the compositions of the present invention.

Suitably the use of the third aspect provides a colour having excellent wash fastness.

The present invention offers significant advantages over methods of dyeing eyebrows of the prior art.

The composition is easy to apply and has a fast development time. It is flexible to use because an operator can easily return to any areas of the brows that have been missed and add more product.

The present invention has also been found to provide longer lasting staining of the skin and longer lasting dyeing of the brow hairs than methods of the prior art. Furthermore because the compositions of the present invention do not comprise oxidative dyes or require the use of an oxidising agent, they are not sensitisers and do create and allergenic response. Thus a patch test is not needed prior to use. In addition there are no limits on how often the composition can be applied.

The invention will now be further described with reference to the following non-limiting examples:

EXAMPLE 1

An eyebrow colouring composition was prepared comprising the following components:

| Composition | |
|---|---|
| Ingredient (wt %) | |
| CI Acid black 1 | 1 |
| CI Acid orange 7 | |
| CI Acid red 33 | |
| Ethanol | 20 |
| Lactic acid | 4.0 |
| Benzyl alcohol | 10 |
| Tylose | 1.5 |
| Sodium hydroxide | to pH 3.5 |
| Water | balance |

To prepare the composition water was heated to 55 to 65° C. and tylose was added and stirred until a smooth gel had formed.

After allowing to cool to room temperature, lactic acid, ethanol and benzyl alcohol were added and the mixture was stirred well.

The dyes were added and the mixture stirred for at least 1 hour until the dyes had dispersed evenly.

The pH of the composition was adjusted to 3.5 by the addition of sodium hydroxide.

EXAMPLE 2

The composition of example 1 is applied to eyebrows using an angled brush. The form of the composition allowed it to be precisely applied, with a focus on areas of the brows that are missing brow hairs.

After 2 to 10 minutes (depending on depth required) the composition is wiped off the brows with a wet cotton wool pad or wipe. The eyebrows can then be shaped as required.

Figure 1A:
FIG. 1A shows eyebrows prior to treatment according to the present invention.
Figure 1B:
FIG. 1B shows the same eyebrows after treatment.
Figure 2A:
FIG. 2A shows the eyebrow of a first user before treatment.

FIG. 1A shows eyebrows prior to treatment according to the present invention. FIG. 2A shows the same eyebrows after treatment.

EXAMPLE 3

An eyebrow colouring composition was prepared comprising the following components:

| Composition | |
|---|---|
| Ingredient | Wt % |
| Acid Green 25 | 1 |
| Acid Violet 43 | |
| Acid Red 14 | |
| Acid Yellow 3 | |
| Food Yellow 3 | |
| benzyl alcohol | 7.5 |
| ethanol | 20 |
| citric acid | 2 |
| phenoxyethanol | 0.7 |
| tylose | 1.2 |
| Heliogel (RTM) | 0.5 |
| Sodium hydroxide | to pH 3.5 |
| Water | balance |

EXAMPLE 4

The composition of example 3 was applied to the eyebrow as described in example 2.

Figure 2B:
FIG. 2B shows the eyebrow of the first user after treatment.

FIG. 2A shows the eyebrow of a first user before the treatment, FIG. 2B shows the eyebrow of the first user after treatment.

Figure 3A:
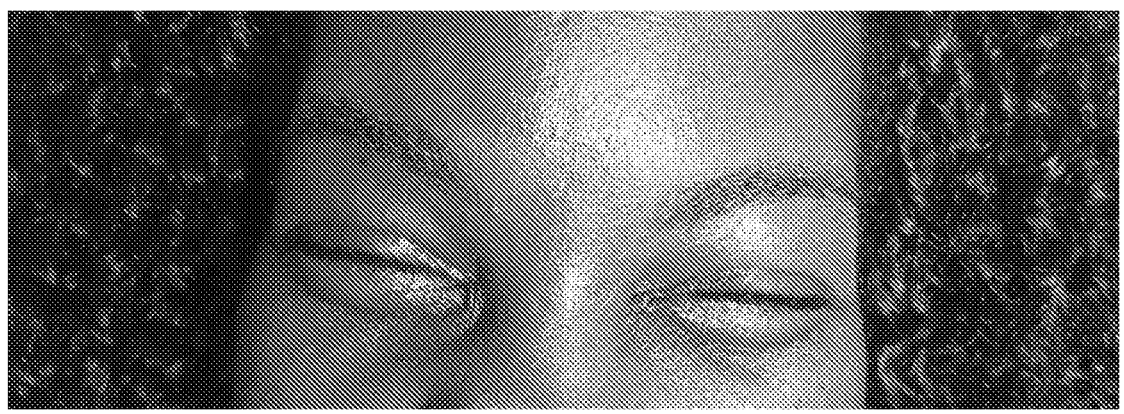
FIG. 3A shows the eyebrow of a second user before treatment.
Figure 3B:
FIG. 3B shows the eyebrow of the second user after treatment.

FIG. 3A shows the eyebrow of a second user before the treatment, FIG. 3B shows the eyebrow of the second user after treatment.

The invention claimed is:

1. A method of colouring an eyebrow, the method comprising:
   (i) contacting the eyebrow with a colouring composition comprising:
      (a) 0.1 to 5 wt % of one or more dye compound containing at least one sulfonate group, at least one carboxylate group, or both;
      (b) 0.1 to 5 wt % citric acid;
      (c) 5 to 10 wt % benzyl alcohol; and
      (d) 10 to 30 wt % ethanol,
   wherein the colouring composition stains the hairs of an eyebrow and the skin therebetween and the colouring composition is an aqueous composition comprising at least 60 wt % water.

2. A method according to claim 1 wherein the one or more dye compound is water soluble.

3. A method according to claim 1 wherein the colouring composition has a pH of 2 to 5.

4. A method according to claim 1 wherein the colouring composition further comprises urea.

\* \* \* \* \*